United States Patent
Okihara

(10) Patent No.: US 10,828,384 B2
(45) Date of Patent: Nov. 10, 2020

(54) MEDICAL DEVICE PACKAGING CONTAINER, MEDICAL DEVICE PACKAGING, AND OUTER CYLINDER PACKAGING FOR PRE-FILLED SYRINGES

(71) Applicant: TERUMO KABUSHIKI KAISHA, Tokyo (JP)

(72) Inventor: Hitoshi Okihara, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/937,114

(22) Filed: Mar. 27, 2018

(65) Prior Publication Data

US 2018/0207308 A1 Jul. 26, 2018

Related U.S. Application Data

(63) Continuation of application No. PCT/JP2016/078654, filed on Sep. 28, 2016.

(30) Foreign Application Priority Data

Sep. 29, 2015 (JP) ................. 2015-192066

(51) Int. Cl.
*A61M 5/00* (2006.01)
*A61L 2/26* (2006.01)
(Continued)

(52) U.S. Cl.
CPC . *A61L 2/26* (2013.01); *A61J 1/00* (2013.01); *A61L 2/07* (2013.01); *A61M 5/00* (2013.01);
(Continued)

(58) Field of Classification Search
CPC ....... A61B 50/33; A61M 5/001; A61M 5/002; A61M 5/008; B01L 2300/0851; B01L 9/06
See application file for complete search history.

(56) References Cited

U.S. PATENT DOCUMENTS 2,812,231 A 11/1957 Zar
5,628,427 A * 5/1997 Hayes .................. A47J 36/022
220/573.1
(Continued)

FOREIGN PATENT DOCUMENTS

CN 103298504 A 9/2013
CN 103562082 A 2/2014
(Continued)

OTHER PUBLICATIONS

WO2014002938_translation.2.pdf (Year: 2014).*
(Continued)

*Primary Examiner* — Allan D Stevens
(74) *Attorney, Agent, or Firm* — Foley & Lardner LLP

(57) ABSTRACT

A medical device packaging container housing a medical device and being configured for high pressure steam sterilization includes: a main body part that includes an open upper face part and a bottom part, wherein the upper face part includes a lid member fixing part for attachment of a peelable sheet-shaped lid member; and a water dispersion part disposed in a peripheral part of the bottom part along a side wall of the main body part, and being configured to disperse water stored in the peripheral part.

12 Claims, 11 Drawing Sheets

(51) Int. Cl.
   *A61L 2/07*     (2006.01)
   *A61J 1/00*     (2006.01)
   *B65D 81/24*    (2006.01)
   *B65D 25/10*    (2006.01)
   *B65D 77/20*    (2006.01)
   *B65D 81/26*    (2006.01)

(52) U.S. Cl.
   CPC ............ *A61M 5/002* (2013.01); *A61M 5/008* (2013.01); *B65D 25/108* (2013.01); *B65D 77/2024* (2013.01); *B65D 81/24* (2013.01); *B65D 81/261* (2013.01); *A61L 2202/24* (2013.01); *A61M 2209/06* (2013.01)

(56) References Cited

U.S. PATENT DOCUMENTS

| | | | |
|---|---|---|---|
| 7,963,396 B2 * | 6/2011 | Vanderbush | A61M 5/002 206/366 |
| 2013/0284632 A1 | 10/2013 | Carrel | |
| 2014/0190861 A1 * | 7/2014 | Carrel | A61M 5/002 206/518 |
| 2015/0374729 A1 * | 12/2015 | Glauber | A01N 47/44 424/409 |

FOREIGN PATENT DOCUMENTS

| | | | |
|---|---|---|---|
| CN | 104602664 A | 5/2015 | |
| JP | 2002-505921 A | 2/2002 | |
| JP | 2011-101681 A | 5/2011 | |
| JP | 2012-071046 A | 4/2012 | |
| JP | 5366010 B2 | 9/2013 | |
| JP | 2013-538627 A | 10/2013 | |
| JP | 2014-505542 A | 3/2014 | |
| JP | 2014-517741 A | 7/2014 | |
| JP | 5714284 B2 | 5/2015 | |
| WO | WO-99/45984 A1 | 9/1999 | |
| WO | WO-2014002938 A1 * | 1/2014 | ............ A61M 1/02 |
| WO | WO-2014/049715 A1 | 4/2014 | |
| WO | WO-2014102987 A1 * | 7/2014 | ............ A61M 5/002 |

OTHER PUBLICATIONS

WO2014102987_translation.pdf (Year: 2014).*
International Search Report with English translation and Written Opinion issued in International Application No. PCT/JP2016/078654 dated Dec. 20, 2016.
Office Action and Search Report dated Apr. 26, 2020 for corresponding Chinese Patent Application No. 201680056691.4.
Supplementary European Search Report dated Mar. 27, 2019 for corresponding European Patent Application No. 16851648.

* cited by examiner

MEDICAL DEVICE PACKAGING CONTAINER, MEDICAL DEVICE PACKAGING, AND OUTER CYLINDER PACKAGING FOR PRE-FILLED SYRINGES

CROSS-REFERENCE TO RELATED APPLICATIONS

The present application is a bypass continuation of PCT Application No. PCT/JP2016/078654, filed on Sep. 28, 2016, which claims priority to Japanese Application No. 2015-192066, filed on Sep. 29, 2015. The contents of these application are hereby incorporated by reference in their entirety.

BACKGROUND

The present disclosure relates to a medical device packaging container that can be sterilized under high pressure steam while housing a medical device; and a medical device packaging and an outer cylinder packaging for pre-filled syringes, which both use the medical device packaging container.

BACKGROUND ART

There are many medical devices that can be sterilized under high pressure steam, such as an outer cylinder for a pre-filled syringe, a pre-filled syringe, an extracorporeal circulation circuit, an infusion set, and a blood transfusion set. Generally, these medical devices are housed in a container with an upper opening, and further are sterilized under high pressure steam in a state where the upper face of the container is sealed with a sheet-shaped lid member having steam permeability.

Further, in recent years, in the preparation of a pre-filled syringe, it has become common to fill a purchased syringe with a medicine without self-preparing the syringe. For this reason, it is required to prepare a syringe (in particular, an outer cylinder for a pre-filled syringe) before being filled with a liquid medicine or the like, and for this purpose, it is required to transport the outer cylinder for a pre-filled syringe. Moreover, it is desired that the pre-filled syringe outer cylinder to be prepared has been sterilized, and if it is unsterilized, sterilization is required to be performed before preparation.

Therefore, a sterilizable or sterilized package housing a plurality of outer cylinders for pre-filled syringes is provided.

The applicant of the present application has proposed an outer cylinder packaging for pre-filled syringes in JP 2012-71046 A. The outer cylinder packaging for pre-filled syringes 1 in JP 2012-71046 A is provided with a container 2; an outer cylinder holding member 4 holding a plurality of outer cylinders 6 for pre-filled syringes, which is housed in the container; and a sheet-shaped lid member 3 that seals the upper opening of the container and can be peeled off. The container has an opening part 22 provided in the bottom part, and a permeable sealing member 5 for sealing the opening part. The permeable sealing member has bacteria impermeability and further steam flowability, and the inside of the container communicates with the outside via the permeable sealing member.

In addition, a packaging has been proposed in JP 2013-538627 A (U.S. Pat. No. 8,939,288, WO 2012-042291). The packaging in JP 2013-538627 A is provided with a grouping nest (5) for receiving the syringes (2), a packaging tub (6), and a sealing cover (8) for sealing the packaging tub. The packaging is provided with a plate (7) intended to be positioned closed to flanges (2a) of syringe bodies (2) before sealing of the tub (6). This plate (7) is provided with at least a first surface (7a) intended to be placed in contact with the flanges (2a) and at least a second surface (7b) located on the side of the cover plate (7) opposite this first surface (7a). The distance between the first surface (7a) and the second surface (7b) is chosen in such a way that, when the first surface (7a) lies against the flanges (2a), the second surface (7b) is in contact or in close proximity of the sealing cover (8).

SUMMARY

In JP 2012-71046 A and JP 2013-538627 A, during high pressure steam sterilization, the steam introduced into a sterilizing tank passes through a sealing member (sheet-shaped lid member) for sealing the opening part of the packaging container and enters the container, and by the incoming heated steam, the medical device housed in the container is sterilized. When the incoming steam touches a side wall having a low temperature or a medical instrument to be sterilized, the steam condenses and turns into water. In particular, the water attached to the side wall flows down along the side wall toward the bottom of the container. In a case in which the bottom of the container is not perfectly horizontal, the flowed-down water gathers in one place and turns into a puddle. If such a puddle is formed, it takes time to dry after sterilization, and residual water may be generated.

In the container in JP 2012-71046 A, an opening part arranged in the bottom part, and a permeable sealing member for sealing the opening part are provided. Therefore, the transpiration of the water retained in the bottom face of the container is favorable. However, water may still accumulate in a peripheral part of the bottom face of the container, as compared with the one in JP 2013-538627 A.

Accordingly, one object of certain embodiments described herein is to provide a medical device packaging container capable of being sterilized under high pressure steam, in which transpiration of the water retained in a peripheral part of a bottom face of the packaging container after high pressure steam sterilization is made favorable, and the water is very unlikely to remain in the peripheral part of the bottom part of the container at the time of use. Another object is to provide a medical device packaging and an outer cylinder packaging for pre-filled syringes that use the medical device packaging container.

According to one embodiment, a medical device packaging container housing a medical device and being configured for high pressure steam sterilization is provided. The packaging container has durability and a shape retaining property to high pressure steam sterilization. The packaging includes a main body part including an open upper face part and a bottom part, the upper face part includes a lid member fixing part for attachment of a peelable sheet-shaped lid member, and the packaging container further comprises a water dispersion part being disposed in a peripheral part of the bottom part along a side wall of the main body part, and configured to disperse water stored in the peripheral part.

In another embodiment, a medical device packaging includes the above-described medical device packaging container; a medical device housed in the container; and a sheet-shaped lid member fixed to the lid member fixing part of the container, sealing the upper face part, and further being peelable and having steam permeability. The medical device packaging is sterilizable under high pressure steam or has been sterilized under high pressure steam.

In another embodiment, an outer cylinder packaging for pre-filled syringes includes the above-described medical device packaging container; a pre-filled syringe outer cylinder housed in the container; and a sheet-shaped lid member being fixed to the lid member fixing part of the container, sealing the upper face part, and further being peelable and having steam permeability. The outer cylinder packaging for pre-filled syringes is sterilizable under high pressure steam or has been sterilized under high pressure steam.

DETAILED DESCRIPTION

Figure 1:
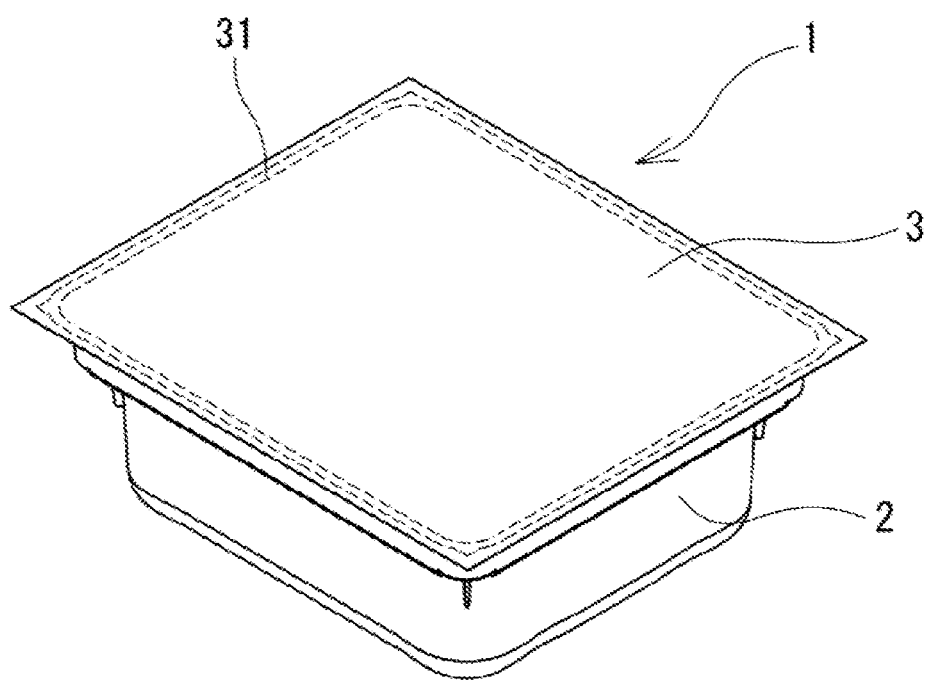
FIG. 1 is a perspective view of an embodiment in which the medical device packaging is applied to an outer cylinder packaging for pre-filled syringes.

Hereinafter, a medical device packaging container capable of being sterilized under high pressure steam, and a medical device packaging and an outer cylinder packaging for pre-filled syringes that use the medical device packaging container will be described by way of embodiments illustrated in the drawings.

The medical device packaging container 2 for high pressure steam sterilization according to one embodiment is a medical device packaging container for housing a medical device (outer cylinder for a pre-filled syringe) 6, and that is sterilized under high pressure steam. The medical device packaging container 2 has high pressure steam sterilization durability and a shape retainable property, and includes a main body part 21 having an open upper face part and a bottom part 27. The upper face part is provided with a lid member fixing part 25 for attachment of a sheet-shaped lid member that can be peeled off. Further, the medical device packaging container 2 has a water dispersion part that is provided in a peripheral part 28 of the bottom part 27 along a side wall of the main body part 21, and can disperse the water retained in the peripheral part 28. In other words, the packaging container 2 has a water dispersion part provided in a peripheral part 28 of the bottom part 27 along a side wall of the main body part 21, in order to disperse the water retained in the peripheral part 28.

The embodiment illustrated in FIGS. 1 to 11 is a medical device packaging using the medical device packaging container 2, and further is an embodiment of an outer cylinder packaging for pre-filled syringes applying the medical device packaging container 2. In addition, a medical device housed in a medical device packaging container or a medical device packaging is not limited to an outer cylinder for a pre-filled syringe, and any medical device may be used as long as it is a medical device that can be sterilized under high pressure steam. For example, a medical device such as a medical container for filling with a medicine, for example, a vial bottle; an extracorporeal circulation circuit (specifically, a dialysis circuit, and a circuit for heart-lung machine); an infusion set; and a blood transfusion set can be mentioned.

An outer cylinder packaging for pre-filled syringes 1 that is a medical device packaging of the embodiment is provided with the above-described medical device packaging container 2 for high pressure steam sterilization, a medical device (specifically, a pre-filled syringe outer cylinder) 6 housed in the container 2, and a sheet-shaped lid member 3 that is fixed to a lid member fixing part of the container 2, seals the upper face part, and further can be peeled off and has steam permeability. Further, the outer cylinder packaging for pre-filled syringes 1 of the present embodiment is an outer cylinder packaging for pre-filled syringes that can be sterilized under high pressure steam or has been sterilized under high pressure steam.

Figure 2:
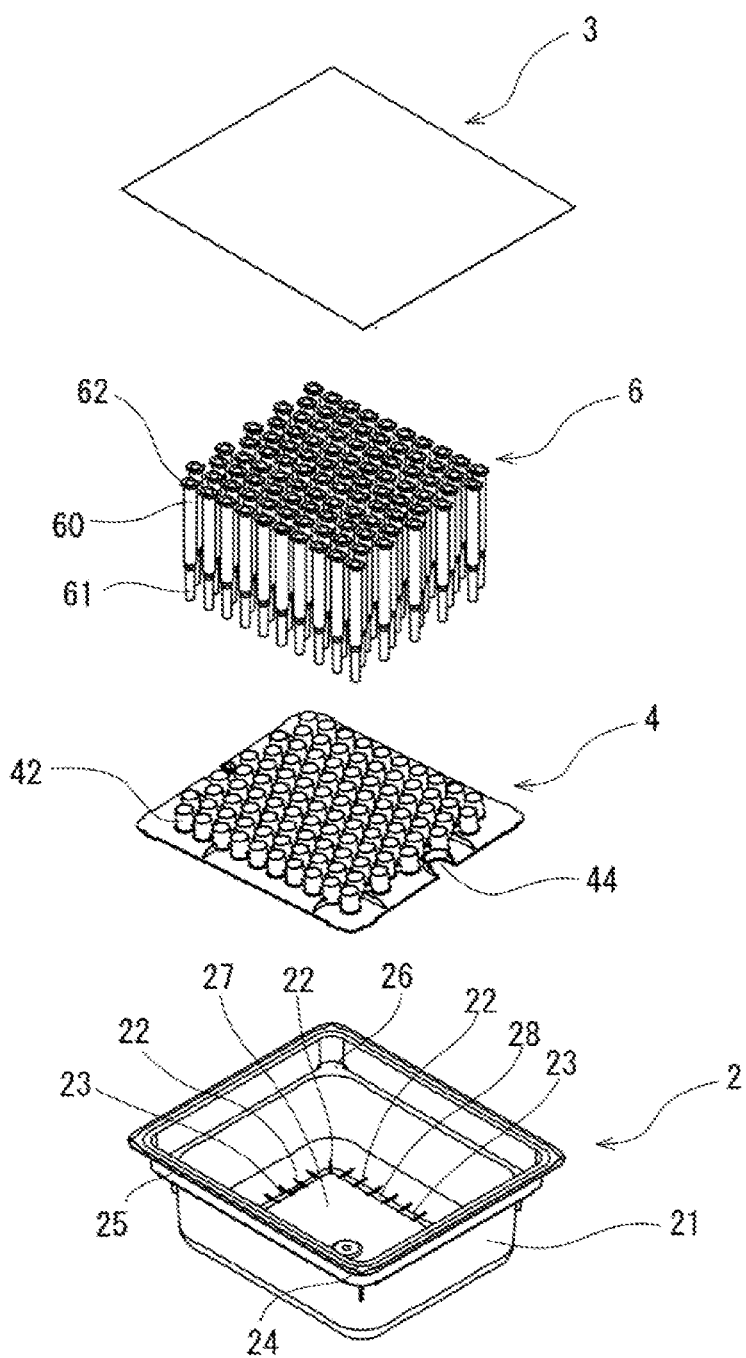
FIG. 2 is an explanatory drawing for explaining an internal configuration of the outer cylinder packaging for pre-filled syringes that is illustrated in FIG. 1.
Figure 3:
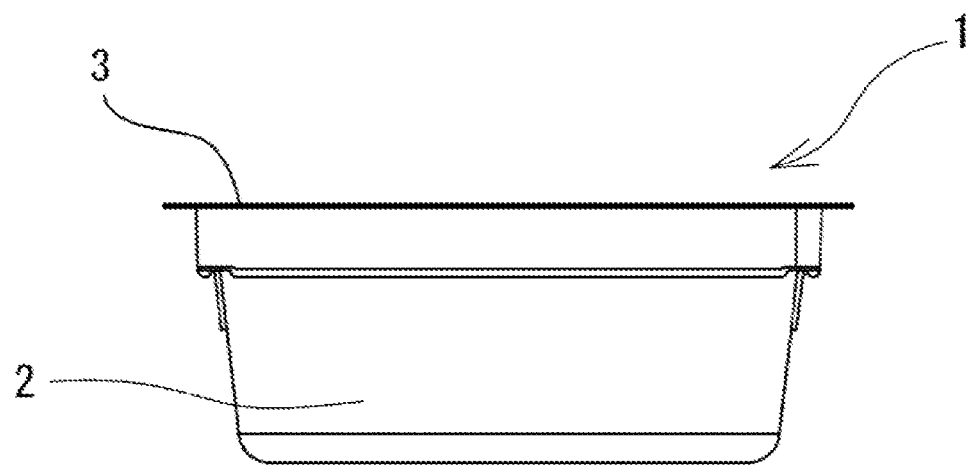
FIG. 3 is a front view of the outer cylinder packaging for pre-filled syringes that is illustrated in FIG. 1.
Figure 4:
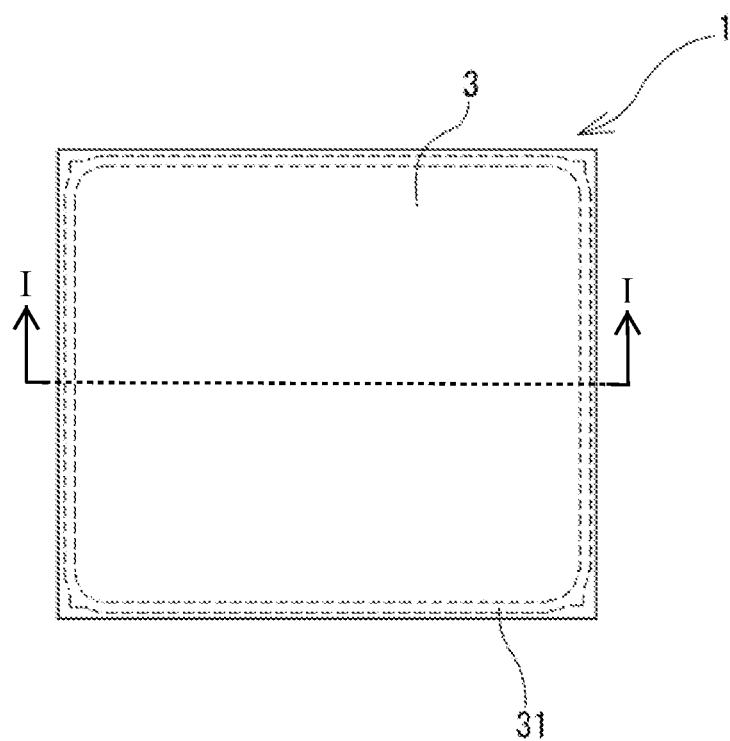
FIG. 4 is a plan view of the outer cylinder packaging for pre-filled syringes that is illustrated in FIG. 3.
Figure 5:
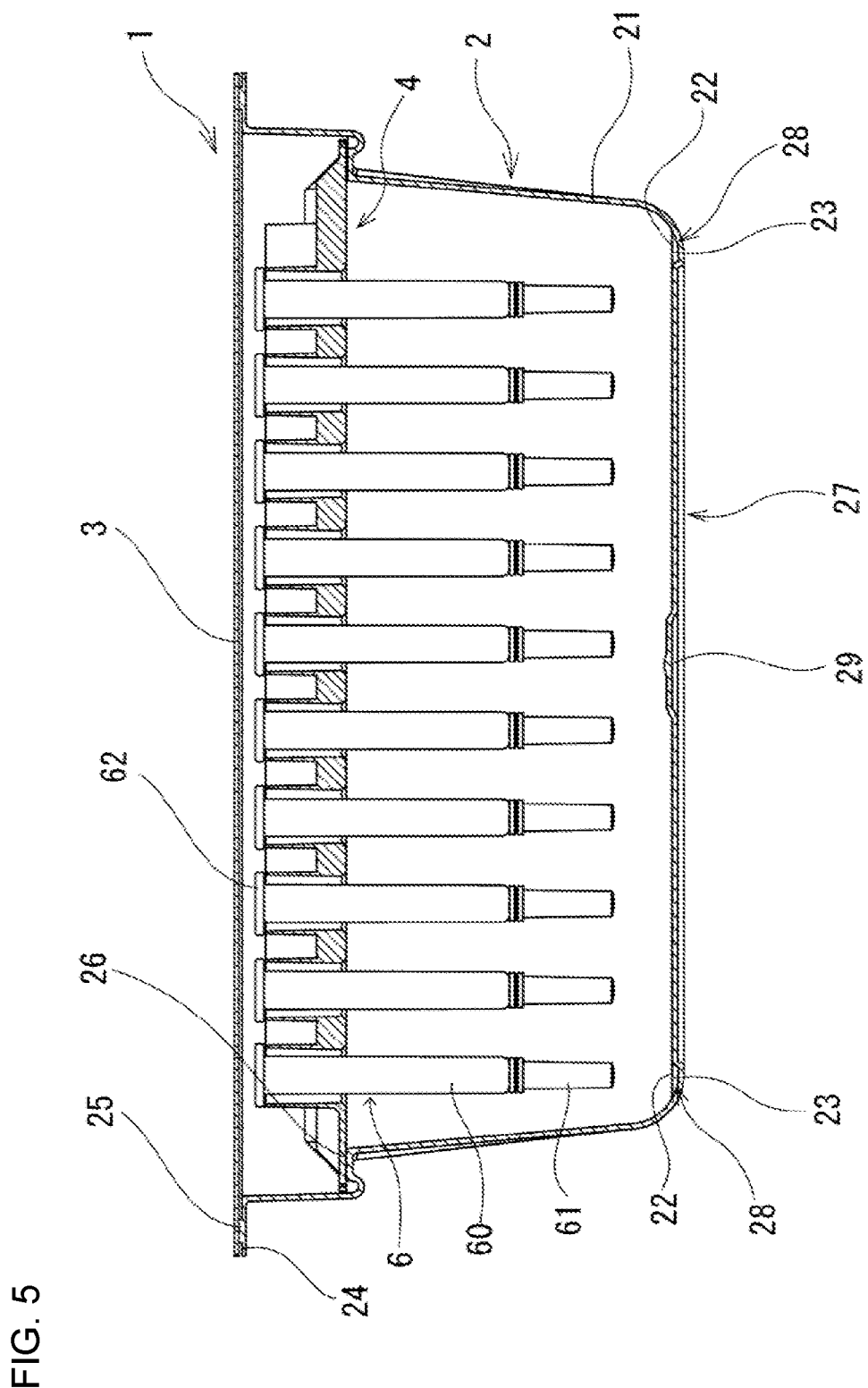
FIG. 5 is an enlarged cross-sectional view taken along a line I-I of FIG. 4.

As illustrated in FIGS. 1, 2 and 5, the outer cylinder packaging for pre-filled syringes 1 is provided with a packaging container 2, an outer cylinder holding member 4 that can hold a plurality of outer cylinders 6 for pre-filled syringes, the plurality of outer cylinders 6 for pre-filled syringes that are held by the outer cylinder holding member 4, and a sheet-shaped lid member 3 that seals the upper opening of the packaging container 2 airtightly and can be peeled off.

As illustrated in FIGS. 1 to 8, the packaging container 2 has a tray shape with a predetermined depth, and has a certain level of strength and a shape retainable property, and is provided with a main body part 21; an outer cylinder holding member holding part 26 for holding a peripheral part of the outer cylinder holding member 4 that holds a pre-filled syringe outer cylinder, which is formed in an upper part of the main body part 21; an annular flange part 24 that is provided along the upper opening, and a peripheral part 28 that is provided in a bottom part 27 of the main body part 21. In particular, in the packaging container 2 of the embodiment, the peripheral part 28 in the bottom part 27 is an annular concave part.

Figure 6:
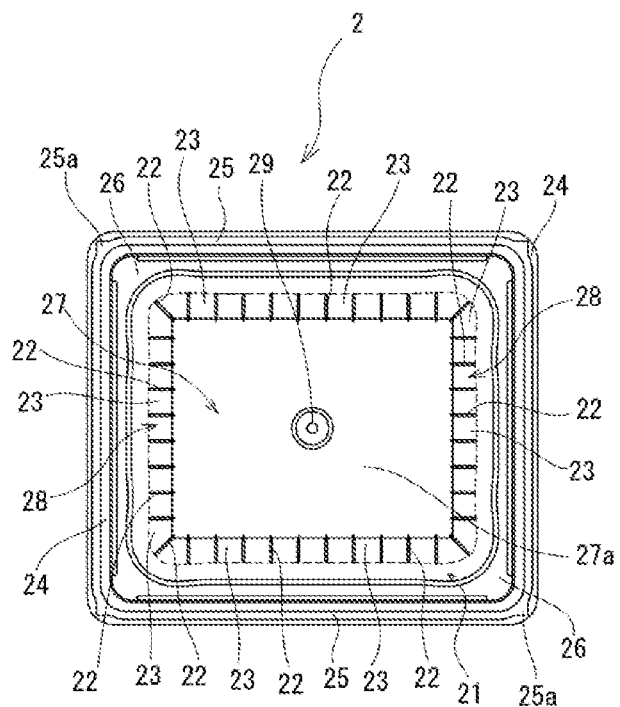
FIG. 6 is a plan view of a medical device packaging container of an embodiment used in the outer cylinder packaging for pre-filled syringes that is illustrated in FIG. 3.
Figure 7:
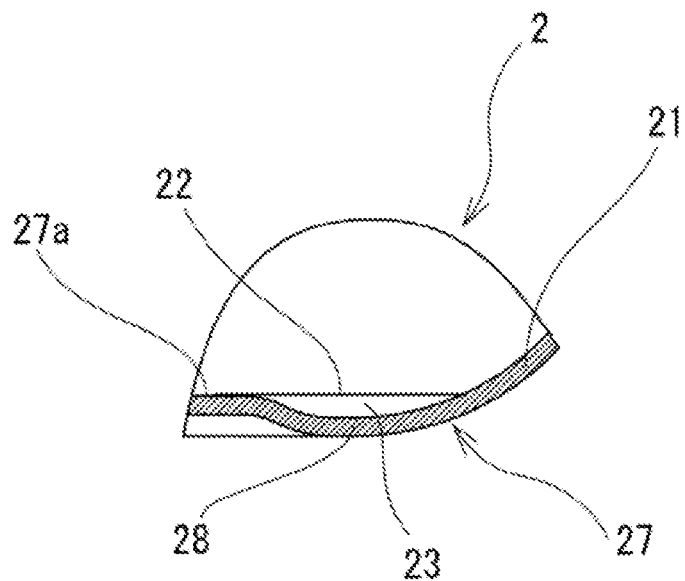
FIG. 7 is an explanatory drawing for explaining a peripheral part in a bottom part of the medical device packaging container that is illustrated in FIG. 6.

As illustrated in FIGS. 6 and 7, the packaging container 2 in the embodiment is a cage-like body having a rectangular shape, and is provided with a thin plate-shaped annular flange part 24 that is formed so as to extend annularly and outwardly on the opening at the upper end. Further, on the upper face of the annular flange part 24, a lid member fixing part 25 that is an annular heat-sealing convex part to be fixed with a sheet-shaped lid member 3 is provided. The annular lid member fixing part 25 is provided such that the entire annular lid member fixing part is inside the outer edge of the annular flange part 24. Further, the annular lid member fixing part 25 is provided such that the entire annular lid member fixing part is outside the inner edge of the annular flange part 24. Furthermore, at the corner part of the annular lid member fixing part 25, a protrusion part 25a extending in the corner part direction of the annular flange part 24 is formed.

In addition, in a position that has a distance of a predetermined length from the flange part 24 to a bottom face, an outer cylinder holding member holding part 26 is formed. In the packaging container 2 in this embodiment, the outer cylinder holding member holding part 26 is an annular step difference part, on which a peripheral part of an outer cylinder holding member 4 that holds outer cylinders for pre-filled syringes can be placed. Further, the outer cylinder holding member holding part is not annularly continuous but may be discontinuous.

Further, the medical device packaging container 2 has a water dispersion part that is provided in a peripheral part 28 of the bottom part 27 along a side wall of the main body part 21, and can disperse the water retained in the peripheral part 28. Specifically, the medical device packaging container 2 has a water dispersion part provided over the entire peripheral part 28, along the annular lower end of the side wall of the main body part 21.

Figure 8:
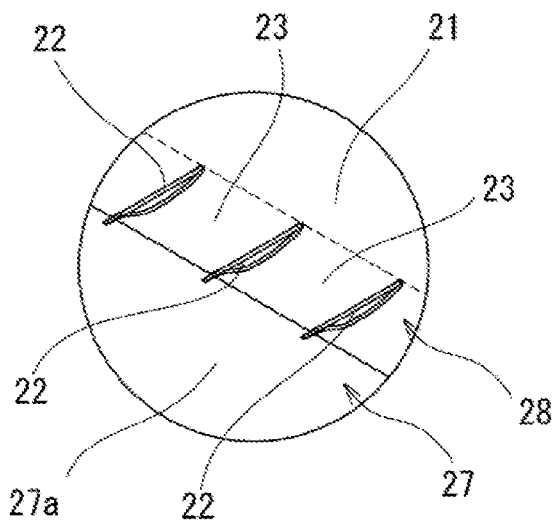
FIG. 8 is an explanatory drawing for explaining a peripheral part in a bottom part of the medical device packaging container that is illustrated in FIG. 6.
Figure 9:
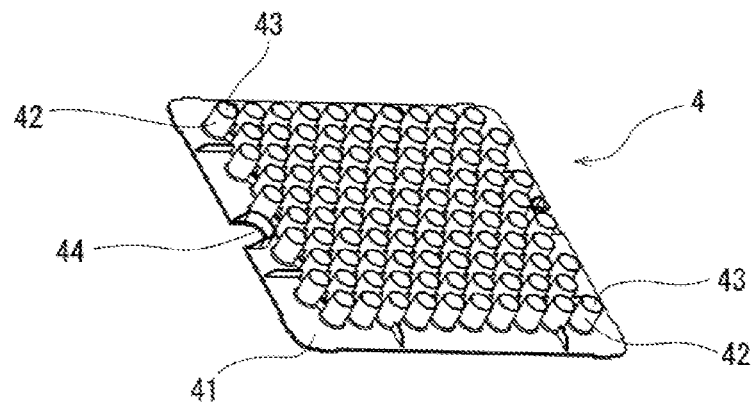
FIG. 9 is a perspective view of an outer cylinder holding member used in the outer cylinder packaging for pre-filled syringes that is illustrated in FIG. 3.
Figure 10:
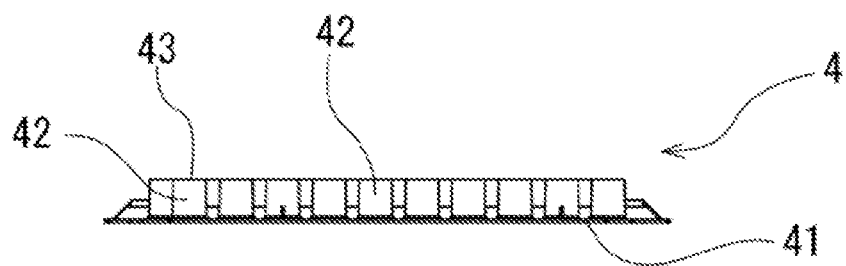
FIG. 10 is a front view of the outer cylinder holding member that is illustrated in FIG. 9.
Figure 11:
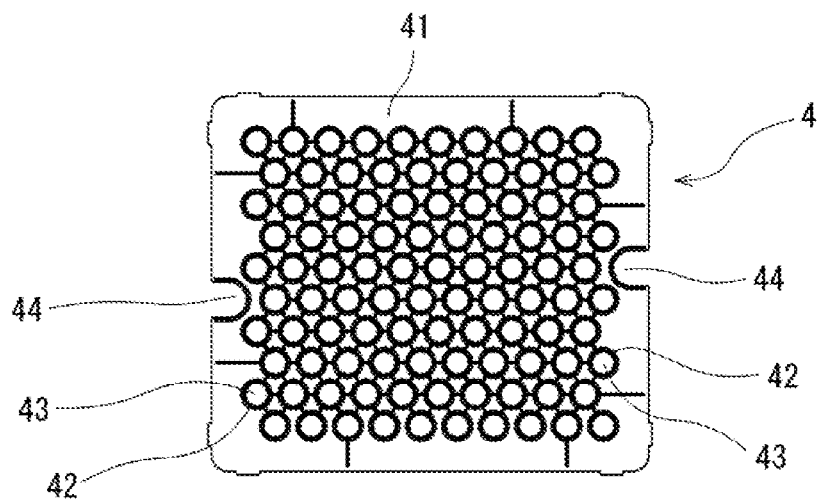
FIG. 11 is a plan view of the outer cylinder holding member that is illustrated in FIG. 9.

In particular, in the embodiment as illustrated in FIGS. 6 to 8, the water dispersion part is formed of a plurality of concave parts 23 provided in a peripheral part 28 of a bottom part 27. As described above, by providing a plurality of concave parts 23 in the peripheral part 28, the water to be retained in the peripheral part is dispersedly retained in the plurality of concave parts, so that a large puddle of water is not formed. In the container 2 in this embodiment, a plurality of concave parts 23 are formed so as to surround a flat part (central part) 27a of the bottom part 27 and are adjacent to each other.

In addition, as illustrated in FIGS. 7 and 8, the packaging container 2 in this embodiment has an annular concave part provided in a peripheral part 28 of a bottom part 27, and further, is provided with a plurality of ribs 22 that are arranged so as to cross the annular concave part from the outer edge toward inner edge of the annular concave part, in other words, so as to dam the annular concave part. Further, the plurality of concave parts 23 are formed by partitioning the annular concave part with a plurality of ribs 22. As described above, by providing a plurality of ribs 22 so as to cross the annular concave part, a sufficient number of concave parts 23 can be formed, and the area of the upper face of each concave part 23 becomes sufficiently small. In addition, with these a plurality of ribs 22 crossing the annular concave part, the reinforcing action of the bottom part is further exerted. Further, in the container 2 in this embodiment, only thin ribs 22 and concave parts 23 are provided in the peripheral part of the bottom part 27, and only ribs 22 are provided in the part where concave parts 23 are not formed.

In addition, in the container 2 in this embodiment, a rib 22 is provided such that one end of a rib 22 is positioned on a flat part 27a and the other end reaches a side wall of the main body part 21 crossing the annular concave part. Therefore, a higher reinforcing effect is exerted. Further, in conformity with the annular concave part provided in a peripheral part 28, the peripheral part protrudes downwardly in the lower face of the bottom part 27. As a result, when placing a packaging container 2 on a mounting table of a sterilizer for high pressure steam sterilization, the contact area between the lower face of the bottom part 27 and the mounting table is decreased, and the condensed water generated along with high pressure steam sterilization is unlikely to accumulate between the lower face of the bottom part 27 and the mounting table, and as a result, the drying time after the sterilization becomes shortened. Further, the shape of the concave part 23 is not limited to the above-described one, and a concave part having a circular or polygonal shape may be accepted. In addition, in the container 2 in this embodiment, a protrusion part 29 for reinforcement is provided in the central part of the bottom part 27. Further, the concave part 23 may be provided in the entire bottom part of the container 2.

Specifically, as to the depth of the annular concave part, the distance between the flat part 27a surrounded by the annular concave part and the lowermost part of the annular concave part in the bottom part 27 is preferably from 0.5 to 10 mm, and in particular, is preferably from 1.0 to 3.0 mm. Further, the width of the annular concave part is preferably from 5 to 50 mm, and in particular, is preferably from 15 to 30 mm. In addition, the area of the upper face of each concave part 23 is preferably from 25 to 1600 $mm^2$, and in particular, is preferably from 50 to 300 $mm^2$. Further, the number of the concave parts 23 formed in a peripheral part 28 is preferably from 2 to 60, and in particular, is preferably from 32 to 48. Moreover, the interval of ribs 22 (distance between the ribs adjacent to each other) is preferably from 5 to 100 mm, and in particular, is preferably from 5 to 15 mm. In addition, the width of the rib 22 is preferably from 0.3 to 3 mm, and in particular, is preferably from 0.5 to 1.0 mm.

Further, as illustrated in FIG. 7, in the container 2 in this embodiment, specifically, the upper end of the rib 22 is positioned above the flat part 27a surrounded by the annular concave part in the bottom part 27. In this embodiment, the rib 22 protrudes upward from the flat part 27a of the bottom part 27 although the protruding of the rib 22 is extremely slight. Therefore, the flow of water between the concave parts 23 can be reliably inhibited.

As the packaging container 2, it is preferred to have a certain level of a shape retainable property and rigidity. Further, in order to cope with the high pressure steam sterilization, a thermoplastic material having heat resistance (120° C. or more) is preferably used for the packaging container 2. Examples of the material that has a certain level of a shape retainable property, a certain level of rigidity, heat resistance, and thermoplasticity include polyolefin such as polypropylene, and polyethylene, a vinyl chloride resin, a polystyrene/polypropylene resin, polyethylene/ionomer (for example, ethylene-based, styrene-based and fluorine-based)/polyethylene, a polyester resin (for example, polyethylene terephthalate, polybutylene terephthalate, and amorphous polyethylene terephthalate), and PP/EVOH/PP (a laminate). The thickness of the packaging container 2 in this case is preferably from about 0.05 mm to about 4.00 mm, and in particular, is more preferably from 1.00 mm to 2.00 mm.

Figure 12:
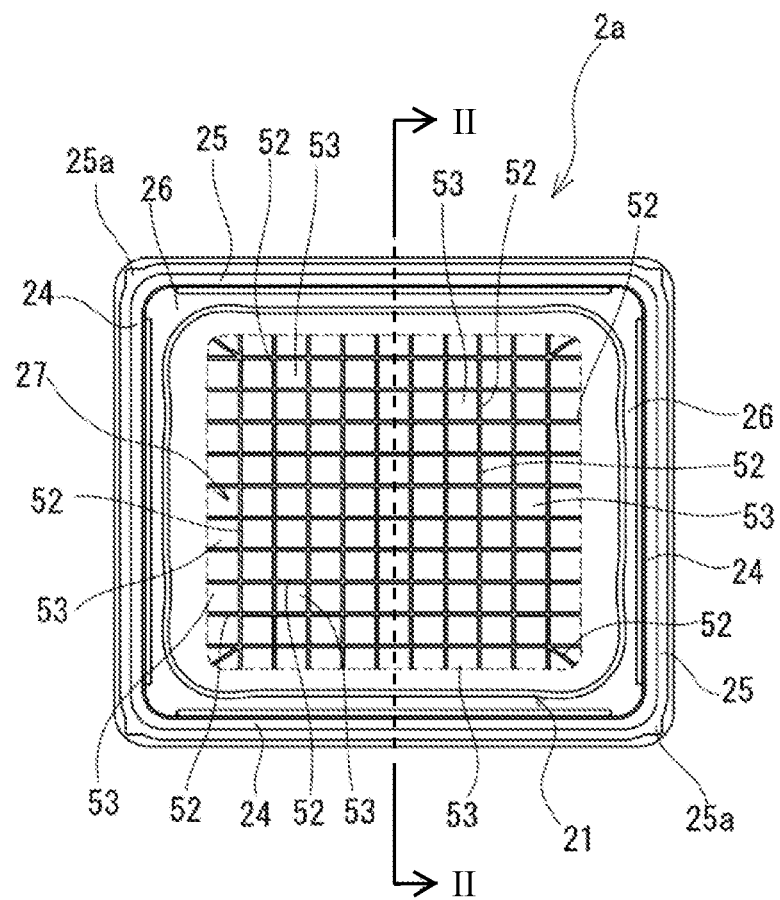
FIG. 12 is a plan view of a medical device packaging container of another embodiment.
Figure 13:
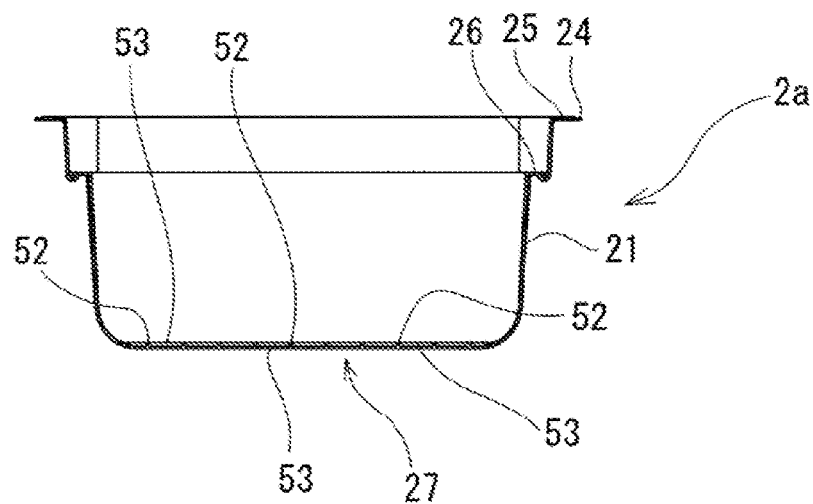
FIG. 13 is a cross-sectional view taken along a line II-II of FIG. 12.

In addition, the form of the water dispersion part provided in a peripheral part in a bottom part of the packaging container may be a type of the form provided in the packaging container 2a illustrated in FIGS. 12 and 13.

The packaging container 2a in this embodiment has no annular concave part in a peripheral part of a bottom part 27, but has a grid-like rib 52 provided on the upper face of at least a peripheral part 28 of the bottom part 27. Further, with the grid-like rib 52, a plurality of concave parts 53 are formed. In particular, in the packaging container 2a in this embodiment, the grid-like rib 52 is formed in the entire bottom part 27, and the concave parts 53 are also formed in the entire bottom part 27. Note that the grid-like rib 52 may also be provided only in a peripheral part of the bottom part 27. Further, in this embodiment, the peripheral part may also be an annular concave part.

The height of the grid-like rib 52 and the depth of the concave part 53 is preferably from 1.0 to 10 mm, and in particular, is preferably from 1.5 to 4.0 mm. Each of the transverse width and longitudinal width of the concave part 53 is preferably from 5 to 40 mm, and in particular, is preferably from 10 to 20 mm. Further, the area of the upper face of each concave part 53 is preferably from 25 to 1600 mm$^2$, and in particular, is preferably from 100 to 400 mm$^2$. In addition, the number of the concave parts 53 formed in a peripheral part is preferably from 4 to 80, and in particular, is preferably from 28 to 48. Moreover, the interval of ribs 52 (distance between the ribs adjacent to each other) is preferably from 5 to 40 mm, and in particular, is preferably from 10 to 20 mm. Further, the width of the rib 52 is preferably from 0.5 to 3.0 mm, and in particular, is preferably from 1.0 to 2.0 mm.

Figure 14:
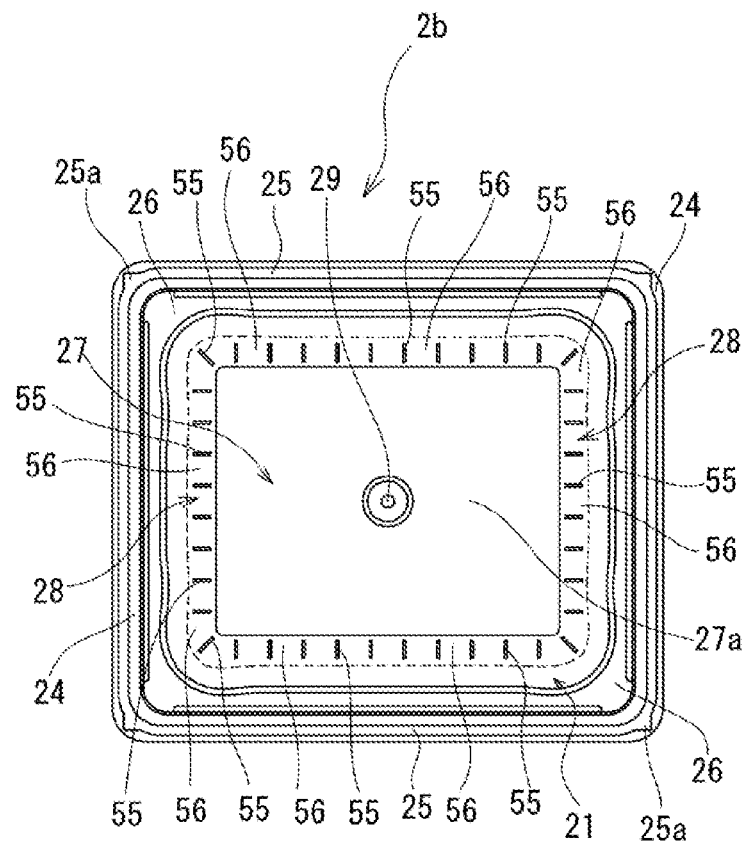
FIG. 14 is a plan view of a medical device packaging container of another embodiment.
Figure 15:
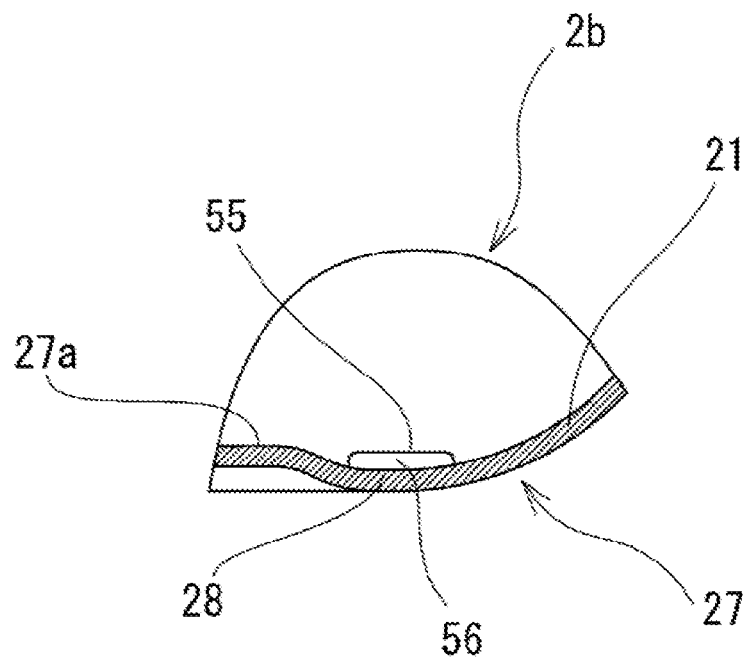
FIG. 15 is an explanatory drawing for explaining a peripheral part in a bottom part of the medical device packaging container that is illustrated in FIG. 14.
Figure 16:
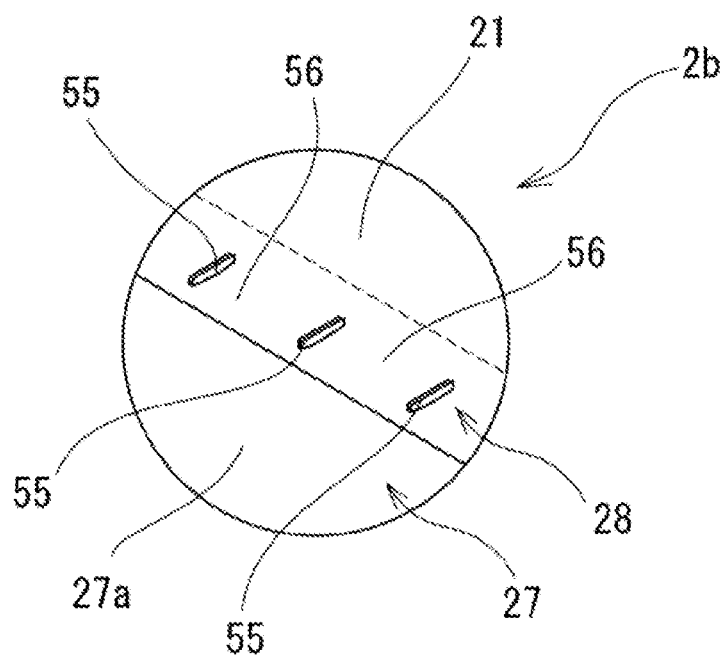
FIG. 16 is an explanatory drawing for explaining a peripheral part in a bottom part of the medical device packaging container that is illustrated in FIG. 14.

In addition, the form of the water dispersion part provided in a peripheral part in a bottom part of the packaging container may be a type of the form provided in the packaging container 2b illustrated in FIGS. 14 to 16.

The water dispersion part that is provided in the packaging container 2b in this embodiment is formed of a plurality of ribs provided in a peripheral part 28 in a bottom part 27. Specifically, the water dispersion part is formed of an annular concave part provided in a peripheral part 28 of a bottom part 27, and a plurality of ribs 55 that are provided in an annular concave part without partitioning the annular concave part, and can disperse the water retained in the annular concave part. In this embodiment, the annular concave part is not partitioned, and the entire annular concave part is communicated. However, in the central part in the annular concave part, a large number of ribs 55 extending a predetermined length in a direction of crossing the annular concave part (specifically, crossing from the outer edge toward inner edge of the annular concave part) without partitioning the annular concave part. Therefore, the annular concave part has a large number of non-flowing parts 56 formed between ribs 55 in the central part of the annular concave part. Further, since the annular concave part has the non-flowing part 56, the annular concave part is communicated in both side parts of the non-flowing part. The rib 55 functions as a baffle plate formed in the annular concave part and inhibits the flow of water.

The depth of the annular concave part, specifically, the distance between the flat part 27a surrounded by the annular concave part and the lowermost part of the annular concave part in the bottom part 27 is preferably from 0.5 to 10 mm, and in particular, is preferably from 1.0 to 3.0 mm. Further, the width of the annular concave part is preferably from 5 to 50 mm, and in particular, is preferably from 15 to 30 mm. In addition, the protrusion height of the rib 55 from the bottom face of the annular concave part is preferably from 1.0 to 10 mm, and in particular, is preferably from 1.5 to 3.0 mm. Moreover, the length of the rib 55 is preferably from 3/10 to 9/10, and in particular, is preferably from 5/10 to 8/10 of the width of the annular concave part. Further, the number of the ribs 55 formed in a peripheral part 28 is preferably from 2 to 60, and in particular, is preferably from 32 to 48. In addition, the interval of ribs 55 (distance between the ribs adjacent to each other) is preferably from 5 to 50 mm, and in particular, is preferably from 15 to 30 mm. Moreover, the width of the rib 55 is preferably from 0.3 to 3.0 mm, and in particular, is preferably from 0.5 to 1.0 mm.

Figure 17:
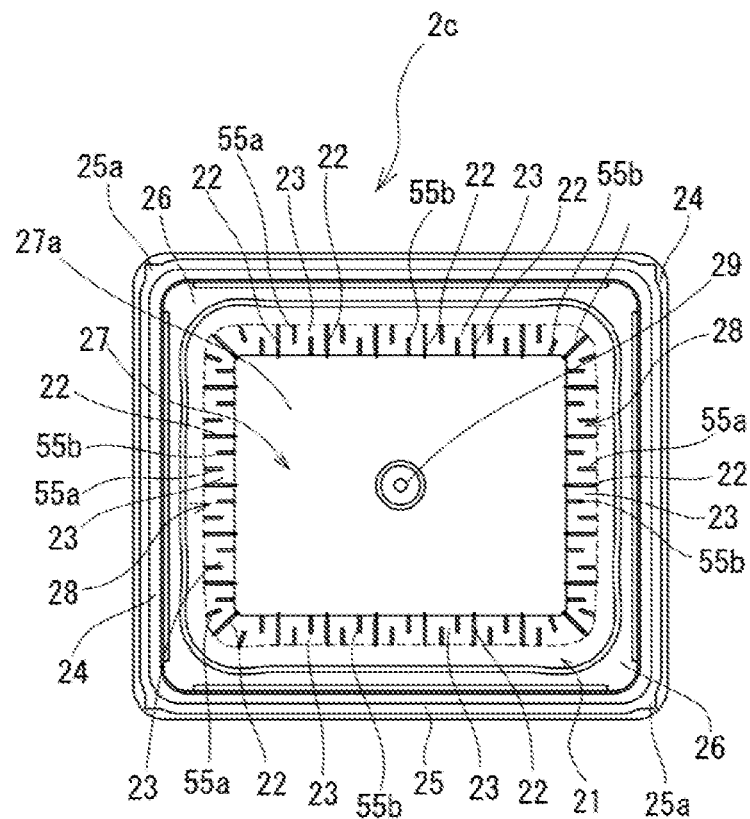
FIG. 17 is a plan view of a medical device packaging container of another embodiment.
Figure 18:
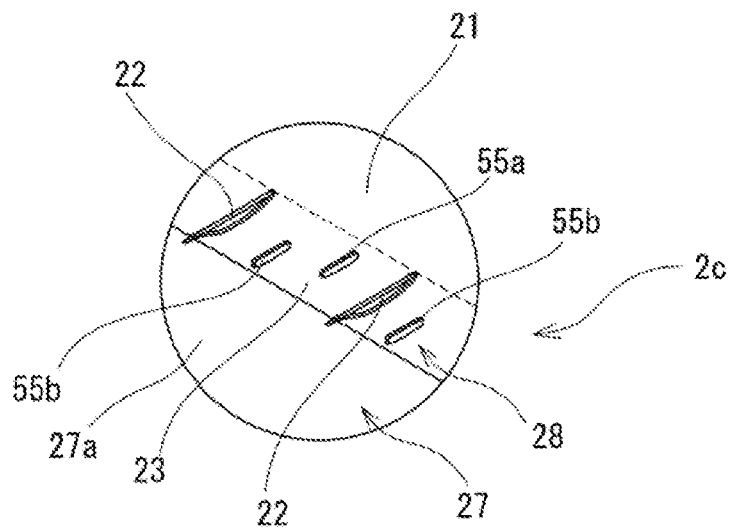
FIG. 18 is an explanatory drawing for explaining a peripheral part in a bottom part of the medical device packaging container that is illustrated in FIG. 17.

In addition, the form of the water dispersion part provided in a peripheral part in a bottom part of the packaging container may be a type of the form provided in the packaging container 2c illustrated in FIGS. 17 and 18.

The packaging container 2c in this embodiment has the same basic configuration as that shown in FIGS. 6 and 7 and described above, and further is provided with ribs 55a and 55b that are arranged inside the plurality of concave parts 23, and do not partition the concave part 23.

As illustrated in FIGS. 17 and 18, the packaging container 2c in this embodiment has an annular concave part provided in a peripheral part 28 of a bottom part 27, and further, is provided with a plurality of ribs 22 that are arranged so as to cross the annular concave part from the outer edge toward inner edge of the annular concave part, in other words, so as to dam the annular concave part. Further, the plurality of concave parts 23 are formed by partitioning the annular concave part with a plurality of ribs 22. In addition, in the concave part 23 partitioned with ribs 22, ribs 55a and 55b that do not partition the concave part 23 are provided.

With this arrangement, the formation of a puddle of water in concave part 23 is inhibited. In particular, in the container 2c in this embodiment, inside the concave part 23, a lateral side rib 55a that extends a predetermined length in the center direction of a bottom part 27 from a side wall of a main body part 21, the side wall forming a concave part 23, and does not reach a flat plate part 27a of the bottom part 27 of the concave part 23; and an inside rib 55b that extends a predetermined length in the side wall direction of the main body part 21 from the flat plate part 27a of the bottom part 27, and does not reach the side wall are provided. Therefore, the concave part 23 is a meandering concave part. As described above, by providing concave-inside ribs 55a and 55b that do not partition the concave part 23, the formation of a puddle of water in the concave part 23 is inhibited.

In this embodiment, the ribs 22, 55a, and 55b reinforce the bottom part 27. Further, in the container 2c in this embodiment, only thin ribs 22, 55a, and 55b, and concave parts 23 are provided in a peripheral part of the bottom part 27, and only ribs 22, 55a, and 55b are provided in the part where concave parts 23 are not formed.

The depth of the annular concave part, specifically, the distance between the flat part 27a surrounded by the annular concave part and the lowermost part of the annular concave part in the bottom part 27 is preferably from 0.5 to 10 mm, and in particular, is preferably from 1.0 to 3.0 mm. Further, the width of the annular concave part is preferably from 5 to 50 mm, and in particular, is preferably from 15 to 30 mm. In addition, the area of the upper face of each concave part 23 is preferably from 25 to 1600 mm$^2$, and in particular, is preferably from 50 to 300 mm$^2$. Further, the number of the concave parts 23 formed in a peripheral part 28 is preferably from 2 to 60, and in particular, is preferably from 32 to 48. Moreover, the interval of ribs 22 (distance between the ribs 22 adjacent to each other) is preferably from 5 to 100 mm, and in particular, is preferably from 5 to 15 mm. In addition, the width of the ribs 22, 55a, and 55b is preferably from 0.3 to 3.0 mm, and in particular, is preferably from 0.5 to 1.0 mm. Further, the distance between the rib 22 and the concave-inside rib 55a or 55b that is adjacent to the rib 22 is preferably from 0.5 to 2.0 mm, and in particular, is preferably from 1.0 to 1.5 mm. Furthermore, the distance between the concave-inside ribs 55a and 55b that are adjacent to each other is preferably from 0.5 to 2.0 mm, and in particular, is preferably from 1.0 to 1.5 mm.

Figure 19:
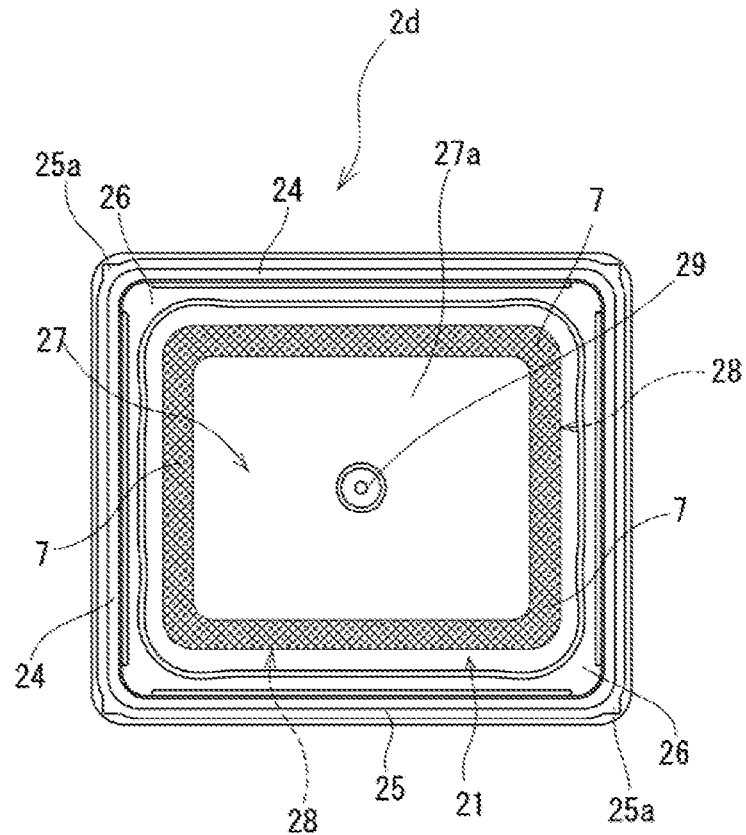
FIG. 19 is a plan view of a medical device packaging container of another embodiment.
Figure 20:
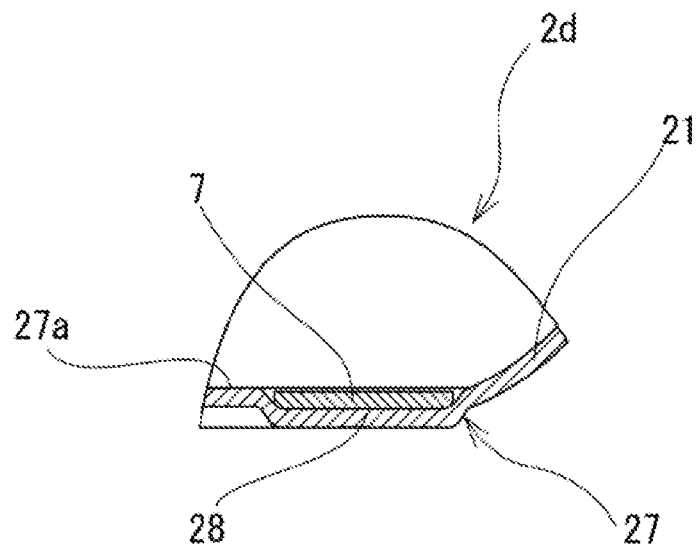
FIG. 20 is an explanatory drawing for explaining a peripheral part in a bottom part of the medical device packaging container that is illustrated in FIG. 19.

In addition, the form of the water dispersion part provided in a peripheral part in a bottom part of the packaging container may be a type of the form provided in the packaging container 2d illustrated in FIGS. 19 and 20.

The water dispersion part that is provided in the packaging container 2d in this embodiment is formed of a sheet 7 having a large number of voids and placed on an upper face of a peripheral part 28 in a bottom part 27. Specifically, in the packaging container 2d, the water dispersion part is formed of an annular concave part provided in the peripheral part 28 of the bottom part 27, and an annular sheet 7 having a large number of voids and placed on an upper face of the annular concave part. In the container 2d in this embodiment, the bottom part 27 is provided with an annular and flat plate-like concave part that is formed in the peripheral part 28, and further has a bottom face formed into a flat face, and extends annularly with a predetermined width. In addition, an annular sheet 7 is placed on an upper face of the annular concave part so as to fill the annular concave part. The depth of the annular concave part, specifically, the distance between the flat part 27a surrounded by the annular concave part and the lowermost part of the annular concave part in the bottom part 27 is preferably from 0.5 to 10 mm, and in particular, is preferably from 1.0 to 3.0 mm. Further, the thickness of the annular sheet 7 is preferably from 0.5 to 10 mm, and in particular, is preferably from 1.0 to 3.0 mm. In this regard, the annular sheet 7 may be fixed to the annular concave part by dotted welding or the like.

As the annular sheet 7, a sheet having a large number of voids and allowing the entry of the inside water is used. As the sheet 7, a mesh-like sheet, sponge, cloth, or the like is preferred. Further, as the sheet 7, a sheet having no water absorbency is preferred. As the sheet described above, various kinds of sponges having open cells, mesh formed of synthetic fibers or natural fibers (for example, a honeycomb mesh sheet), a cloth such as woven fabric or nonwoven fabric, a porous membrane, or the like is used. As the sponge having open cells, there are, for example, natural rubber sponge, synthetic rubber sponge, and plastic foam. Examples of the synthetic rubber for the synthetic rubber sponge include silicone rubber, poly urethane rubber, styrene-butadiene rubber (SBR), butadiene-acrylonitrile rubber (BA), chloroprene rubber (CR), ethylene-propylene rubber (EPM-EPDM), butadiene rubber (BR), butyl rubber (IIR), and isoprene rubber (IR). Examples of the plastic for the plastic foam include polyethylene, ethylene vinyl acetate copolymer, polypropylene, propylene copolymer, polystyrene, polyurethane, polyvinyl chloride, and acrylic resin. The open cell preferably has a pore diameter of from 0.05 to 0.1 mm in view of the water permeability, the cross-sectional shape is not particularly limited, and examples the cross-sectional shape include a circle, an ellipse, a square, a rectangle, and an indefinite shape, and further the shape in the thickness direction of the porous support is also not particularly limited, and examples the shape include a linear shape, a curved shape, and a zigzag shape.

In addition, as an embodiment of the packaging container, a container not having an annular concave part in the bottom part may also be accepted. In this case, the sheet forming the water dispersion part does not have an annular shape, and may have a shape having an outer shape along the peripheral part of the bottom part. Also, in the embodiment as described above, the outer edge of the sheet exists along the peripheral part of the bottom part, therefore, the water dispersion part is formed in the peripheral part of the bottom part.

The sheet-shaped lid member 3 covers and seals the upper end opening part of the packaging container 2, and further is peelable from the packaging container 2. The sheet-shaped lid member 3 has bacteria impermeability and steam flowability, and further can peelably seal the packaging container 2.

As the sheet-shaped lid member 3, any member may be used as long as it has bacteria impermeability and steam flowability. Further, as the sheet-shaped lid member 3, a member with which the packaging container 2 can be heat-sealed is preferred. As the sheet-shaped lid member 3 described above, for example, a non-woven fabric made of a synthetic resin, specifically, a non-woven fabric made of a synthetic resin material such as polyolefin, which is known as TYVEK (registered trademark), a porous film made of a synthetic resin, or the like can be suitably used. Further, as the sheet-shaped lid member 3, in order to facilitate the heat sealing of the sheet-shaped lid member 3 to the packaging container 2, a member having a peripheral part on which a resin for heat sealing has been applied may be used.

In addition, the sheet-shaped lid member 3 is fixed on the heat-sealing convex part 25 that is provided in the annular flange part 24 of the packaging container 2 by peelably fixing the peripheral part by the fixing part 31. The fixing part 31 is preferably formed of a heat seal. Further, in this embodiment, the outer edge of the sheet-shaped lid member is not heat-sealed to the outer edge part and inner edge part of the annular flange part 24 of the packaging container 2, so that the sheet-shaped lid member is easily peeled off. Moreover, a protrusion part 25a that is provided at a corner part of the heat-sealing convex part 25 functions as a peeling starting part. As the sheet-shaped lid member 3, the thickness is preferably from about 0.05 mm to about 1.00 mm, and more preferably from about 0.10 mm to about 0.50 mm.

As illustrated in FIGS. 1, 2 and 5, the outer cylinder packaging for pre-filled syringes 1 in this embodiment is provided with an outer cylinder holding member 4 that can hold a plurality of outer cylinders 6 for pre-filled syringes, and the plurality of outer cylinders 6 for pre-filled syringes that are held by the outer cylinder holding member 4.

As illustrated in FIGS. 2, 5, and 9 to 11, the outer cylinder holding member 4 that can hold the plurality of outer cylinders 6 for pre-filled syringes is provided with a substrate part 41, and a plurality of cylindrical parts 42 that each protrudes upward from the substrate part 41. Further, an opening 43 is formed at the upper end of the cylindrical part 42, and a notch part 44 for being gripped is formed in a lateral part of the substrate part 41. Inner diameters of the cylindrical part 42 and the opening 43 are larger than the diameter of a main body part of the outer cylinder 6 for a pre-filled syringe to be held, so that the flange part of the outer cylinder 6 for a pre-filled syringe to be held cannot pass through the cylindrical part 42 and the opening 43.

Accordingly, as illustrated in FIG. 6, the outer cylinder 6 penetrates the cylindrical part 42, and is hung by the flange of the outer cylinder from the opening 43. Further, as illustrated in FIG. 6, the lower end (a tip of a cap member) of the outer cylinder 6 for a pre-filled syringe held by the outer cylinder holding member 4 does not come into contact with the bottom face of the packaging container 2. In other words, the bottom face of the packaging container 2 and the lower end (the tip of the cap member) of the outer cylinder 6 for a pre-filled syringe held by the outer cylinder holding member 4 are separated from each other, so that the flow of steam is not inhibited. In order to cope with the high pressure steam sterilization, the material for forming the outer cylinder holding member 4 desirably has the heat resistance (120° C. or more) as well.

As the outer cylinder 6 for a pre-filled syringe, a known one can be used. The outer cylinder 6 for a pre-filled syringe is provided with an outer cylinder main body 60, and a cap 61 for sealing a nozzle part provided at a tip part of the outer cylinder main body 60. Further, a flange 62 is provided at the proximal part of the outer cylinder main body 60. The flange 62 is an elliptical donut-shaped disk part formed so as to protrude in the perpendicular direction from the entire circumference of the rear end of the outer cylinder main body 60.

Examples of the material for forming the outer cylinder 6 include various kinds of resins such as polypropylene, polyethylene, polystyrene, polyamide, polycarbonate, polyvinyl chloride, poly-(4-methylpentene-1), an acrylic resin, an acrylonitrile-butadiene-styrene copolymer, a polyester such as polyethylene terephthalate, a cyclic olefin polymer, and a cyclic olefin copolymer, and among them, a resin such as polypropylene, a cyclic olefin polymer, and a cyclic olefin copolymer is preferred, because of being easy to mold and having heat resistance.

INDUSTRIAL APPLICABILITY

In certain embodiments, the medical device packaging container is configured as follows.

(1) A medical device packaging container housing a medical device and being for high pressure steam sterilization, in which the packaging container comprises durability and a shape retainable property to high pressure steam sterilization, and a main body part including an open upper face part and a bottom part, the upper face part includes a lid member fixing part for attachment of a peelable sheet-shaped lid member, and the packaging container further comprises a water dispersion part being disposed in a peripheral part of the bottom part along a side wall of the main body part, and configured to disperse water stored in the peripheral part.

In this packaging container, a water dispersion part that can disperse the water retained in a peripheral part of a bottom part of the container is provided, therefore, the water dispersion part inhibits the water that flows down to the bottom part from gathering in one place and forming a puddle, and can disperse the water retained in the peripheral part of the bottom of the packaging container, accordingly, the transpiration of the water becomes favorable. As a result, the water extremely is unlikely to remain in the peripheral part of the bottom part of the container at the time of use.

Further, the above-described embodiment may be additionally configured as follows.

(2) The medical device packaging container for high pressure steam sterilization according to (1) above, in which the water dispersion part is formed of a plurality of concave parts disposed in the peripheral part.

(3) The medical device packaging container for high pressure steam sterilization according to (2) above, in which the bottom part comprises an annular concave part disposed in the peripheral part, and a plurality of ribs disposed so as to cross the annular concave part from an outer edge of the annular concave part toward an inner edge of the annular concave part, and the plurality of concave parts are formed by partitioning the annular concave part by the plurality of ribs.

(4) The medical device packaging container for high pressure steam sterilization according to (2) above, in which the plurality of concave parts are formed so as to surround a central part of the bottom part, and are adjacent to each other.

(5) The medical device packaging container for high pressure steam sterilization according to (1) above, in which the water dispersion part is formed of a plurality of ribs disposed in the peripheral part of the bottom part.

In addition, the medical device packaging is configured as follows.

(6) A medical device packaging, including: the medical device packaging container for high pressure steam sterilization according to any one of (1) to (5) above; a medical device housed in the container; and a sheet-shaped lid member being fixed to the lid member fixing part of the container, sealing the upper face part, and further being peelable and having steam permeability, in which the medical device packaging can be sterilized under high pressure steam or has been sterilized under high pressure steam.

In this medical device packaging, a packaging container to be used has a water dispersion part that can disperse the water retained in a peripheral part of a bottom part of the container, therefore, the water dispersion part inhibits the water that flows down to the bottom part from gathering in one place and forming a puddle, and can disperse the water retained in the peripheral part of the bottom of the packaging container, accordingly, the transpiration of the water becomes favorable. As a result, the water is very unlikely to remain in the peripheral part of the bottom part of the container at the time of use of the medical device packaging.

Further, the outer cylinder packaging for pre-filled syringes may be configured as follows.

(7) An outer cylinder packaging for pre-filled syringes, including: the medical device packaging container for high pressure steam sterilization according to any one of (1) to (5) above; a pre-filled syringe outer cylinder housed in the container; and a sheet-shaped lid member being fixed to the lid member fixing part of the container, sealing the upper face part, and further being peelable and having steam permeability, in which the outer cylinder packaging for pre-filled syringes can be sterilized under high pressure steam or has been sterilized under high pressure steam.

In this outer cylinder packaging for pre-filled syringes, a packaging container to be used has a water dispersion part that can disperse the water retained in a peripheral part of a bottom part of the container, therefore, the water dispersion part inhibits the water that flows down to the bottom part from gathering in one place and forming a puddle, and can disperse the water retained in the peripheral part of the bottom of the packaging container, accordingly, the transpiration of the water becomes favorable. As a result, the water is very unlikely to remain in the peripheral part of the bottom part of the container at the time of use.

Further, the above-described embodiment may be the following product.

(8) The outer cylinder packaging for pre-filled syringes according to (7) above, in which the outer cylinder packaging for pre-filled syringes is provided with an outer cylinder holding member housed in the container.

What is claimed is:

1. A medical device packaging container housing a medical device and being configured for steam sterilization, the packaging container comprising:
    a main body part that comprises:
        an open upper face part, and
        a bottom part,
        wherein the open upper face part comprises a lid member fixing part for attachment of a peelable sheet-shaped lid member,
        wherein the bottom part comprises:
            an annular concave part disposed in a peripheral part of the bottom part along a side wall of the main body part, wherein a width of the annular concave part is in a range of 5 to 50 mm, and a depth of the annular concave part is in a range of 1.0 to 3.0 mm,
            a central part that has rectangular shape and is surrounded by the annular concave part, and
            a plurality of ribs that are disposed in the annular concave part, extend upward from a bottom of the annular concave part, and cross the annular concave part, wherein a width of each of the plurality of ribs is in a range of 0.5 to 1.0 mm, and wherein the plurality of ribs are spaced at intervals each in a range of 5 to 15 mm,
            wherein the annular concave part comprises a plurality of concave parts formed by partitioning the annular concave part with the plurality of ribs, and each of the plurality of concave parts comprises an open upper face that has an area in a range of 50 to 300 mm$^2$.

2. The medical device packaging container according to claim 1, wherein the bottom part further comprises a plurality of concave-inside ribs that extend a predetermined length in a direction crossing the annular concave part without partitioning the annular concave part, so as to function as a baffle plate formed in the annular concave part.

3. A medical device packaging comprising:
    the medical device packaging container according to claim 1;
    the medical device housed in the container; and
    a sheet-shaped lid member that is fixed to the lid member fixing part of the container and seals the open upper face part, the lid member being peelable and having steam permeability;
    wherein the medical device packaging is sterilizable under steam or has been sterilized under steam.

4. An outer cylinder packaging for pre-filled syringes, the outer cylinder packaging comprising:
    a medical device packaging container that comprises a main body part that comprises:
        an open upper face part, and
        a bottom part,
        wherein the open upper face part comprises a lid member fixing part, wherein the bottom part comprises:
            an annular concave part disposed in a peripheral part of the bottom part along a side wall of the main body part, wherein a width of the annular concave part is in a range of 5 to 50 mm, and a depth of the annular concave part is in a range of 1.0 to 3.0 mm,
            a central part that has rectangular shape and is surrounded by the annular concave part, and
            a plurality of ribs that are disposed in the annular concave part, extend upward from a bottom of the annular concave part, and cross the annular concave part, wherein a width of each of the plurality of ribs is in a range of 0.5 to 1.0 mm, and wherein the plurality of ribs are spaced at intervals each in a range of 5 to 15 mm,
            wherein the annular concave part comprises a plurality of concave parts formed by partitioning the annular concave part with the plurality of ribs, and each of the plurality of concave parts comprises an open upper face that has an area in a range of 50 to 300 mm$^2$;
    a plurality of outer cylinders for pre-filled syringes, each of the plurality of outer cylinders comprising a distal end, a proximal end opposite the distal end, and a flange disposed at the proximal end;
    an outer cylinder holding member housed in the container and configured to hold the plurality of outer cylinders, the outer cylinder holding member comprising a substrate part and a plurality of cylindrical parts; and
    a sheet-shaped lid member that is fixed to the lid member fixing part of the container and seals the open upper face part, the lid member being peelable and having steam permeability;
    wherein each of the plurality of outer cylinders is held by a respective one of the plurality of cylindrical parts of the outer cylinder holding member by engaging the flange of the outer cylinder and an upper end of the respective cylindrical part such that the distal end of each of the plurality of outer cylinders faces the bottom part of the main body part.

5. The medical device packaging container according to claim 1, wherein a first end of each of the plurality of ribs is positioned on the central part of the bottom part, and a second end of each of the plurality of ribs reaches the side wall of the main body part.

6. The medical device packaging container according to claim 1, wherein the plurality of ribs protrude upward from the central part of the bottom part.

7. The medical device packaging container according to claim 6, wherein a first end of each of the plurality of ribs is positioned on the central part of the bottom part, and a second end of each of the plurality of ribs protrudes upward from the central part of the bottom part.

8. The medical device packaging container according to claim 1, wherein a first end of each of the plurality of ribs is located inside a periphery of an upper surface of the central part of the bottom part.

9. The medical device packaging container according to claim 1,
    wherein the central part of the bottom part includes a flat central part located above the annular concave part, and
    wherein an upper end of the annular concave part is located at an edge of the flat central part.

10. The medical device packaging container according to claim 9, wherein the bottom part includes a protrusion located in the flat central part.

11. The medical device packaging container according to claim 1, wherein, in a height direction, an upper end of each of the plurality of ribs is above an upper surface of the central part.

12. The outer cylinder packaging for pre-filled syringes according to claim 4, wherein, in a height direction, an upper end of each of the plurality of ribs is above an upper surface of the central part.

\* \* \* \* \*